United States Patent
Nomura

(10) Patent No.: US 7,964,218 B2
(45) Date of Patent: Jun. 21, 2011

(54) GRANULAR PREPARATIONS FOR ORAL ADMINISTRATION

(75) Inventor: Tatsuo Nomura, Tokyo (JP)

(73) Assignee: Mitsubishi Tanabe Pharma Corporation, Osaka ( * ) Notice: Subject to any disclaimer, the term of this patent is extended or adjusted under 35 U.S.C. 154(b) by 801 days.

(21) Appl. No.: 10/363,680

(22) PCT Filed: Sep. 5, 2001

(86) PCT No.: PCT/JP01/07697
§ 371 (c)(1), (2), (4) Date: Jul. 21, 2003

(87) PCT Pub. No.: WO02/19993
PCT Pub. Date: Mar. 14, 2002

(65) Prior Publication Data
US 2004/0101567 A1    May 27, 2004

(30) Foreign Application Priority Data
Sep. 6, 2002 (JP) ................................. 2000-269526

(51) Int. Cl.
*A61K 31/716* (2006.01)
*A61K 9/16* (2006.01)
*A61K 9/50* (2006.01)

(52) U.S. Cl. .......................................... 424/490; 514/57

(58) Field of Classification Search .................. 424/493, 424/497
See application file for complete search history.

(56) References Cited

U.S. PATENT DOCUMENTS 4,999,189 A * 3/1991 Kogan et al. .................. 424/493
5,447,726 A * 9/1995 Nomura ......................... 424/464
6,066,336 A * 5/2000 Ullah et al. .................... 424/480
6,171,618 B1 * 1/2001 Johnson et al. ............... 424/472
6,174,873 B1 * 1/2001 Wrenn, Jr. ..................... 514/45

FOREIGN PATENT DOCUMENTS

| CA | 2009736 | 8/1990 |
| CA | 2040471 | 10/1991 |
| EP | 637447 | 2/1995 |
| EP | 873129 | 10/1998 |
| WO | 98/15265 | 4/1998 |

OTHER PUBLICATIONS

"Grain". Dictionary.com. Jan. 2005. Online. Internet. Accessed on Jan. 25, 2006. <http://dictionary.reference.com/search?q=grain>.*
Safety MSDS data for diethylaminoethanol. Accessed online on Aug. 28, 2008 at http://msds.chem.ox.ac.uk/DI/diethylaminoethanol. html. pp. 1-2.*
Mesh size conversion table (Wikipedia).*
Dow ETHOCEL premium polymers for pharmaceutical applications: product data sheet (Oct. 1998).*
Official Action issued on Sep. 10, 2004 in the corresponding Chinese application, together with English translation thereof.
Z. G. Yang, "Preparation of Pulsatile Controlled-Release Pellets of Theophylline", Pharma. J. Chin. PLA, vol. 16, No. 1, Feb. 2000, with English abstract.
European Office Action issued Aug. 6, 2008 corresponding to European application 01 963 438.5.
Canadian Intellectual Property Office Search Report issued Oct. 22, 2008 in Canadian Application No. 2,421,240 of which the present application corresponds.

* cited by examiner

*Primary Examiner* — Jeffrey S Lundgren
*Assistant Examiner* — Sara E Townsley
(74) *Attorney, Agent, or Firm* — Wenderoth, Lind & Ponack, L.L.P.

(57) ABSTRACT

The present invention provides an oral grain preparation comprising an agent swellable in the mouth as an active component, wherein the preparation has an inner coating layer of a water-soluble cellulose polymer and an outer coating layer of an ethylcellulose on a plain grain having a diameter of 3 to 4 mm. The agent of the present invention is free from sliminess peculiar to cellulose and adherence of each grains in the mouth at taking, and has excellent feeling for taking without an unpleasant feeling such as caused by a large tablet.

12 Claims, 1 Drawing Sheet

GRANULAR PREPARATIONS FOR ORAL ADMINISTRATION

This application is a U.S. national stage of International Application No. PCT/JP01/07697 filed Sep. 5, 2001.

TECHNICAL FIELD

The present invention relates to an oral grain preparation. More specifically, the invention relates to an oral grain preparation having excellent property for easy taking.

BACKGROUND ART

Dry syrups, suspended in situ before administration, have conventionally been commercially available for anion exchange resin preparations which need a large dose. However, the dry syrups are inconvenient, because they take time for administration and require a large single dose. Some tablets have also been studied, however, no research has been made as for a relation between a size or a coating formulation of tablets and a property for easy take. Accordingly, a preparation that achieves higher compliance has been desired.

A tablet containing an anion exchange resin as a major component is required not to disintegrate in the mouth, but to rapidly disintegrate in the body so as to exhibit its efficacy. No published book describes what degree of non-disintegration in the mouth is sufficient. In a design for grains aiming at masking of unpleasant taste of a drug (PHARM TEC JAPAN, VOL. 6, No. 7, p 77 (1990)), practical sensory tests were employed by placing agents in the mouth for about 20 seconds and then spitting out the agents for evaluation with the purpose of prevention of the taste for 20 to 30 seconds. As for coatings of tablets containing an anion exchange resin as an active ingredient, a coating method is known wherein stearic acid is dissolved under heating in polyethylene glycol by using a cholestyramin resin without solvent (Japanese Patent Unexamined Publication (KOKAI) No. (Hei)3-236326). However, the resulting tablets has poor storage stability in open conditions. The tablet will disintegrate within several hours at room temperature, and accordingly, they have a problem of extremely poor stability after being unpacked. Further, the coating film has low strength and a high risk of wear and tear. Therefore, the tablets also have a problem that they suffer from breakage during packaging process or transportation.

In addition, a method is known in which a coating is performed using a solution of hydroxypropylmethylcellulose (Japanese Patent Unexamined Publication (KOKAI) No. (Hei) 7-97330). Tablets coated solely with celluloses will give sliminess due to dissolution of the celluloses on the surface of tablets in the mouth. When a tablet as a dosage has a large size, or several tablets are to be taken, the sliminess may not cause a direct problem in terms of a property for easy taking. However, when a single dosage comprises approximately 50 to 100 grains for easy taking of an anion exchange resin, which requires a large volume dosage, celluloses on the surface of the grain preparations will be dissolved to cause adherence and aggregation of the grain preparations in the mouth, which results in remarkable deterioration of feeling of taking.

DISCLOSURE OF THE INVENTION

The present inventors have made various researches in view of the above problems. As a result, they have found that an oral grain preparation with an excellent property for easy taking, which comprises anion exchange resins as active components, can be obtained by coating plain grains having a diameter of 3 to 4 mm with a solution of a water-soluble cellulose polymer, and further coating with an aqueous dispersion of ethyl cellulose.

BEST MODE FOR CARRYING OUT THE INVENTION

Figure 1:
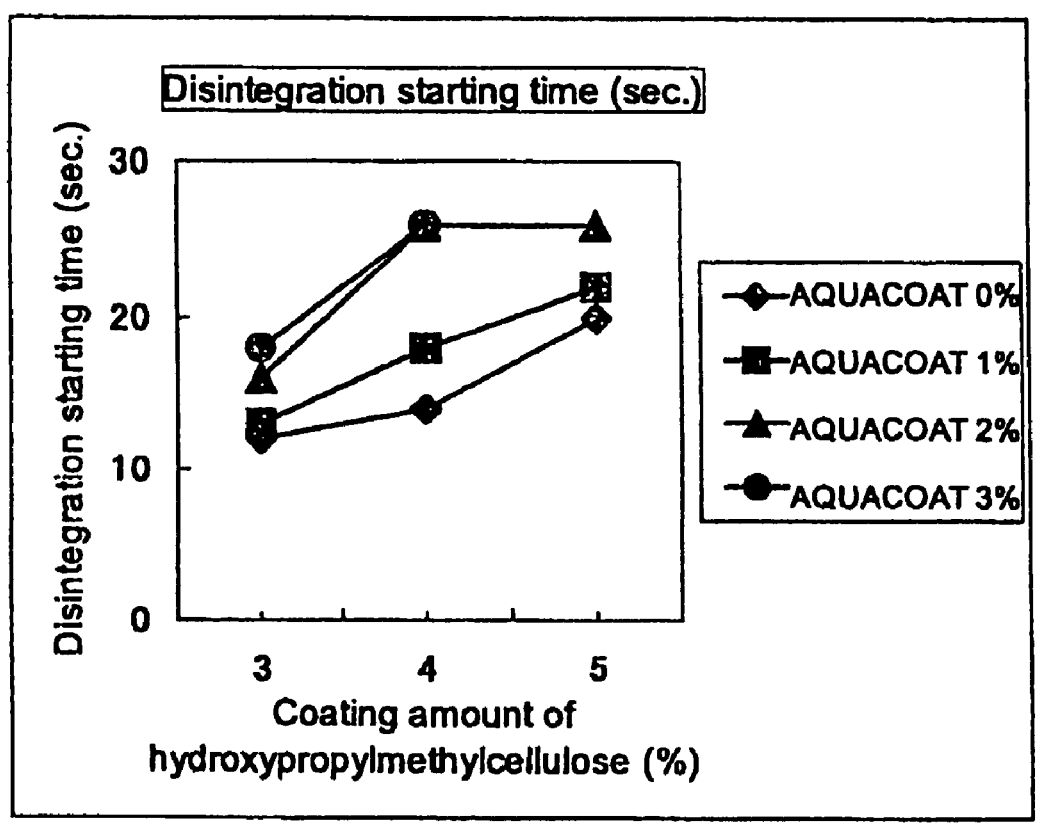
FIG. 1 depicts a relation between the amount of coating in a coated tablet (percent by weight based on the weight of a plain grain) and disintegration starting time (sec.).

The gist of the present invention is an oral grain preparation comprising an anion exchange resin as an active ingredient, which is obtained by coating plain grains having a diameter of 3 to 4 mm with 2 to 8% by weight of water-soluble polymer cellulose solution and 0.5 to 4% by weight of ethyl cellulose aqueous dispersion (for example, trade name "AQUACOAT"; an aqueous dispersion of ethylcellulose, cetanol and sodium lauryl distributed by FMC Biopolymer, also available from Asahi Kasei Corporation and Shin-Etsu Chemical Co., Ltd), wherein the total coating amount is 6 to 8.5% by weight (hereinafter the coating amount will be indicated by "% by weight" based on the weight of the plain grain). A large dosage is required for an anion exchange resin, and if the diameter of grains is as small as 3 to 4 mm, the number of grains for one dosage become as much as about 50 to 100. When a water-soluble cellulose polymer solution is solely used for coating, adherence of each grains in the mouth will occur due to the peculiar sliminess. In general, in order to eliminate the sliminess, 30 to 50% of powdered ethyl cellulose or low-substituted hydroxypropylcellulose is often added before coating to the water-soluble cellulose polymer solution as a coating base material. However, it is known that the addition of such water-insoluble solid components may degrade the strength of the coating film and significantly deteriorates the stability of the tablets under humid conditions (Japanese Patent Unexamined Publication (KOKAI) No. (Hei) 7-97330). The present inventors have found that stable a grain preparation free from sliminess is obtainable by an undercoating with a water-soluble polymer cellulose and further an overcoating with a suitable amount of an ethylcellulose aqueous dispersion. A large amount of coating exceeding 8.5% of the total coating amount will be too much time consuming for coating and not practically applicable in view of the poor productivity. Further, a grain preparation that is coated with 3% by weight of a water-soluble cellulose polymer solution and 4 or 5% of an ethylcellulose aqueous dispersion will generate small cracks on the film which contains a large amount of water-insoluble components, which results in a lowering of film strength.

Furthermore, anion exchange resins have sand-like taste, and disintegration of a preparation in the mouth will remarkably deteriorate a feeling of taking. In other words, high moisture adsorption will swell the preparation, which will cause adhesion to the mucosa in the mouth and difficulty in swallow due to the significant swell in the mouth. Therefore, it is required that no disintegration occurs in the mouth at the time of taking. As a result of the intensive studies, it has been found that disintegration time of a grain preparation can be delayed and controlled by a coating with a water-soluble cellulose polymer solution and an ethylcellulose aqueous dispersion in combination. On the basis of the above findings, the inventors successfully provided a preparation which does not disintegrate in water for 20 to 30 seconds. An oral cholesterol-lowering agent thus obtained is free from an unpleasant feeling at taking such as caused by a large tablet, and the agent needs a smaller dosage than that of granules, attributable to a high density, and gives good feeling of taking.

The gist of the present invention also exists in a method for manufacture of an oral grain preparation, which comprises the following steps:

Step 1: 14 to 20% by weight of water is added and mixed to an anion exchange resin, and then 2% by weight or less of silicon dioxide based on the weight of the anion exchange resin is mixed. After the mixture is recovered, a lubricant is added and the resultant is subjected to tablet compression to obtain a plain grain with a diameter of 3 to 4 mm.

Step 2: The plain grain is coated with 2 to 8% by weight of a water-soluble cellulose polymer solution and then with 0.5 to 4% by weight of an ethylcellulose aqueous dispersion (30% by weight of a solid content).

In the present invention, examples of the agents that swell in the mouth, used as an active ingredient, include anion exchange resins. The anion exchange resins are not particularly limited. A particularly preferred example includes 2-methylimidazole-epichlorohydrin copolymer (hereinafter referred to as "MCI-196") obtained by the method described in Japanese Patent Unexamined Publication (KOKAI) No. (Sho) 60-209523.

Plain grains having a diameter of 3 to 4 mm are prepared by using the active ingredient. The plain grains may be pills and the like, or compressed preparations such as tablets.

From 14 to 20% by weight, preferably 15 to 19% by weight of water is added to the anion exchange resin and mixed. Further, 2% by weight or less, preferably 0.2 to 1.0% by weight of silicon dioxide is added and mixed to the anion exchange resin, and then the resultant mixture is granulated by a speed mill. The granules is added with a lubricant such as hydrogenated oil and mixed, and then compressed using a punch and die having a size of 3 to 4 mm.

The thus prepared plain grains comprising the anion exchange resin are coated with a coating solution containing water-soluble cellulose polymer such as hydroxypropylmethylcellulose by using a coating machine such as High Coater HCT-30 (Freund Industrial Co., Ltd.) under the conditions of, for example, a suction temperature of 80 to 90° C. and a spraying speed of 5 to 10 g/min. In particular, plain grains with a smaller diameter are coated by a coating machine provided with a punching device for granules.

Any water-soluble cellulose polymers may be used as long as they are cellulose polymers that are water-soluble. Hydroxypropylmethylcellulose, hydroxypropylcellulose, and methylcellulose are preferred, and hydroxypropylmethylcellulose is particularly preferred.

Any ethylcellulose aqueous dispersions may be used as long as they are aqueous dispersions containing ethylcellulose. An aqueous dispersion of a latex-type aqueous coating agent containing ethylcellulose as a base material is preferred. An example includes AQUACOAT (trade name, obtained from Asahi Kasei Corporation).

A coating amount of the water-soluble cellulose polymer (hereinafter referred to as "undercoating") is 2 to 8% by weight, and most preferably 4 to 6% by weight. Further, a coating amount of the ethylcellulose aqueous dispersion (hereinafter referred to as "overcoating") is 0.5 to 4% by weight, more preferably 1 to 2% by weigh of, for example, AQUACOAT (trade name, obtained from Shin-Etsu Chemical Co., Ltd.) to carry out the coating.

The oral grain preparations of the present invention have a diameter of 3 to 4 mm, and are free from sliminess peculiar to cellulose. Further, the preparations cause no adherence of each grains in the mouth after taking, and they have excellent feeling of taking without unpleasant feeling caused by large tablets.

A dosage of the oral grain preparation of the present invention is 1 to 10 g, preferably 1.5 to 4 g per day for adult, which may be taken once to three times a day as divided doses before or after meals, or between meals.

The oral grain preparation of the invention may be obtained by coating a plain grain comprising an anion exchange resin having a diameter of 3 to 4 mm with a solution of the water-soluble cellulose polymer at an amount of 3.5 to 8% by weight and then coating the plain grain with an aqueous dispersion of ethylcellulose at an amount of 0.5 to 4% by weight, wherein the total coating amount is 5.5 to 8.5% by weight based on the weight of the plain grain.

The oral grain preparation of the invention may be obtained by coating a plain grain with the solution of the water-soluble cellulose polymer at an amount of 3.5 to 8% by weight and then coating the plain grain with the aqueous dispersion of ethylcellulose at an amount of 0.5 to 4% by weight, wherein the total coating amount is 5.5 to 8.5% by weight based on the weight of the plain grain.

The oral grain preparation of the invention may be obtained by coating a plain grain comprising an anion exchange resin having a diameter of 3 to 4 mm with a solution of the water-soluble cellulose polymer at an amount of 4 to 6% by weight and then coating the plain grain with an aqueous dispersion of ethylcellulose at an amount of 1 to 2% by weight, wherein the total coating amount is 6 to 8% by weight based on the weight of the plain grain.

The oral grain preparation of the invention may be obtained by coating a plain grain with the solution of the water-soluble cellulose polymer at an amount of 4 to 6% by weight and then coating the plain grain with the aqueous dispersion of ethylcellulose at an amount of 1 to 2% by weight, wherein the total coating amount is 6 to 8% by weight based on the weight of the plain grain.

EXAMPLES

The present invention will be explained in more detail by Examples. However, the present invention is not limited to the following examples as long as it does not go beyond the scope thereof.

Example 1

526 g of MCI-196 (water content 5%), 4.5 g of hydroxypropylcellulose, 2.5 g of hydrated silicon dioxide were placed and mixed in a speed kneader (Okada Seiko Co., Ltd.). 52.8 g of purified water was further added for kneading. After recovery, the mixture was granulated by a speed mill (Okada Seiko Co., Ltd.). 1.88 g of hydrogenated oil was added and mixed, and then the resultants were compressed using a compressing machine equipped with a punch and die having a size of 3 mm to obtain plain grains.

The resulting plain grains were subjected to coating using a High Coater HCT-30 under the conditions of 80° C. suction temperature and 5 g/min spraying speed. The coating was carried out in two steps. The first coating solution, whose composition is shown as Formulation 1, was prepared by dissolving hydroxypropylmethylcellulose in water, adding titanium oxide, talc, and polyethylene glycol and well mixing the mixture, and passing the mixture through a sieve of 80 mesh to use for the coating. The coating amount was 4.25% by weight based on the weight of the plain grains. Further, the coating was successively carried out with a coating solution of the composition described as Formulation 2. The coating amount was 2.17% by weight based on the weight of the plain grains. After the coating, 0.12 g of hydrogenated oil was added and polishing was performed.

| Formulation 1: Composition of the undercoating solution | |
|---|---|
| Hydroxypropylmethylcellulose | 4.0% by weight |
| Titanium oxide | 0.5 |
| Talc | 0.5 |
| Polyethylene glycol | 0.8 |
| Purified water | 94.2 |
| Total | 100.0% by weight |

| Formulation 2: Composition of the overcoating solution | |
|---|---|
| Ethylcellulose aqueous dispersion (trade name: AQUACOAT, 30% solid content) | 50.0% by weight |
| Triacetin | 4.5 |
| Purified water | 45.5 |
| Total | 100.0% by weight |

Example 2

Plain grains were prepared in the same manner as in Example 1 and the coating solutions had the same compositions, except the amounts of undercoating and overcoating were changed (each % by weight).

| Undercoating amount | Overcoating amount |
|---|---|
| 4% | 2 and 3% |
| 5% | 1, 2, and 3% |

Comparative Example 1

Plain grains were prepared in the same manner as in Example 1 and the coating solutions had the same compositions, except the amounts of undercoating and overcoating were changed (each % by weight).

| Undercoating amount | Overcoating amount |
|---|---|
| 3% | 0, 1, 2, and 3% |
| 4% | 0 and 1% |
| 5% | 0% |

Comparative Example 2

In Example, plain grains having the diameter of 4.5 mm were prepared. The composition of each coating solution and each coating amount were the same as those in Example 1.

Comparative Example 3

Plain grains were prepared in the same manner as in Example 1. Water-soluble polymer cellulose and ethylcellulose aqueous dispersion were mixed, and according to the composition shown in Formulation 3, 7% by weight of coating was applied to the plain grains.

| Composition 3 | |
|---|---|
| Hydroxypropylmethylcellulose | 4.0% by weight |
| Titanium oxide | 0.5 |
| Talc | 0.5 |
| Ethylcellulose aqueous dispersion (trade name: AQUACOAT, 30% solid content) | 0.0% by weight |
| Triacetin | 4.5 |
| Purified water | 40.5 |
| Total | 100.0% by weight |

Test Example 1

For preparations of Example 2 and Comparative Example 1, starting times of disintegration of each preparations in water were compared. It can be understood that the starting time of disintegration of the preparation in water was remarkably delayed by the undercoating and successive small amount of overcoating according to the present invention. The starting time of disintegration of each preparations shown in FIG. 1 was determined by placing 50 ml of purified water at 37° C. into a 100 ml beaker, adding 6 pieces of the preparation and measuring a time before the break of the coating film. Average values are indicated.

Test Example 2

Sensory evaluations were performed for preparations manufactured in Examples 1 and 2, and Comparative Examples 1 to 3. The following 5 kinds of preparations and commercially available 500 mg tablets were subjected to the sensory evaluation. Preparations B and C correspond to working examples.

TABLE 1

| Type of Preparation | Shape | Undercoating amount | Overcoating amount |
|---|---|---|---|
| Grain preparation A | 3 mm in diameter | 5% | 0% |
| Grain preparation B | 3 mm in diameter | 5% | 1% |
| Grain preparation C | 3 mm in diameter | 4.25% | 2.17% |
| Grain preparation D | 3 mm in diameter | mixed coating 7% | |
| Grain preparation E | 4.5 mm in diameter | 4.25% | 2.17% |
| 500 mg modified tablet | approx. 17 mm of tablet length 7 mm in width | 2.7% | 0% |

The sensory evaluations were performed by employing eight test subjects, each received 2 g dosage (3 tablets only for the 500 mg tablet), for the following items. For the 500 mg tablets, the plain grains were coated at approximately 2.7% by weight using the undercoating formulation (Formulation 1). Three grades were assigned for the sensory evaluation, and as described below, higher scores were given in gradient manner to preferred results. Total scores for each item of the evaluation are summarized in Table 2.
(figures in parentheses indicate the scores)
Appearance (visible appearance); easy for taking (3), slightly difficult for taking (2), and difficult for taking (1)
Sliminess in the mouth; no adhesion (3), adhesion (2), and slight adhesion (1)

Disintegration in the mouth; not fast (3), slightly fast (2), and fast (1)
Swallowability; easy to swallow (3), slightly easy to swallow (2), and difficult to swallow (1)

As a result, the diameter and sliminess of each grain preparation and the tablet had significant effect on the feeling for taking. The evaluation revealed that the diameter of 3 mm was sufficient for easy taking, whilst the diameter of 4.5 mm gave difficulty in taking. Further, when the water-soluble polymer cellulose and the ethylcellulose aqueous dispersion were mixed and subjected to coating of the tablets, sliminess was not eliminated, which indicates necessity of the double coating for elimination of sliminess. The sliminess was eliminated when the overcoating amount was 1% or more by weight.

As shown above, the grain preparations B and C as the working examples gave higher scores than those of the other preparations and thus gave better results.

TABLE 2

| Type of Preparation | Appearance (visible appearance) | Sliminess in the mouth | Disintegration in the mouth | Swallowability | Total |
|---|---|---|---|---|---|
| Grain preparation A | 22 | 8 | 18 | 16 | 64 |
| Grain preparation B | 22 | 22 | 21 | 22 | 87 |
| Grain preparation C | 22 | 24 | 24 | 24 | 94 |
| Grain preparation D | 22 | 10 | 19 | 15 | 66 |
| Grain preparation E | 10 | 24 | 24 | 11 | 69 |
| 500 mg modified tablet | 8 | 20 | 24 | 8 | 60 |

INDUSTRIAL APPLICABILITY

According to the present invention, by applying an inner coating layer of a water-soluble cellulose polymer and an outer coating of ethylcellulose on a plain grain, comprising an anion exchange resin as an active ingredient and having a diameter of 3 to 4 mm, an oral grain preparation can be provided which is free from sliminess, which is peculiar to cellulose, and adherence of each grains in the mouth at taking, and has excellent feeling for taking without an unpleasant feeling such as caused by a large tablet.

The present application was filed claiming the priority on Japanese Patent Application No. 2000-269526.

What is claimed is:

1. An oral grain preparation having a diameter of 3 to 4 mm and comprising an anion exchange resin, wherein the preparation has an inner coating layer of a water-soluble cellulose polymer and an outer coating layer consisting essentially of an ethylcellulose, wherein the oral grain preparation is suitable for oral administration, and wherein the outer layer does not contain a water-soluble cellulose polymer.

2. The oral grain preparation according to claim 1, wherein the anion exchange resin is 2-methylimidazole-epichlorohydrin copolymer.

3. The oral grain preparation according to claim 1, which is obtained by coating a plain grain comprising an anion exchange resin having a diameter of 3 to 4 mm with a solution of the water-soluble cellulose polymer at an amount of 3.5 to 8% by weight and then coating the plain grain with an aqueous dispersion consisting essentially of ethylcellulose at an amount of 0.5 to 4% by weight, wherein the total coating amount is 5.5 to 8.5% by weight based on the weight of the plain grain.

4. The oral grain preparation according to claim 1, which is obtained by coating a plain grain comprising an anion exchange resin having a diameter of 3 to 4 mm with a solution of the water-soluble cellulose polymer at an amount of 4 to 6% by weight and then coating the plain grain with an aqueous dispersion consisting essentially of ethylcellulose at an amount of 1 to 2% by weight, wherein the total coating amount is 6 to 8% by weight based on the weight of the plain grain.

5. The oral grain preparation according to claim 1, wherein the water-soluble cellulose polymer is hydroxypropylmethylcellulose, hydroxypropylcellulose, or methylcellulose.

6. The oral grain preparation according to claim 1, wherein the ethylcellulose is an aqueous dispersion of a latex aqueous coating agent containing ethylcellulose as a base material.

7. An oral grain preparation having a diameter of 3 to 4 mm comprising an anion exchange resin, which is obtained by coating a plain grain comprising an anion exchange resin having a diameter of 3 to 4 mm with a solution of a water-soluble cellulose polymer, and then coating the plain grain with an aqueous dispersion consisting essentially of an ethylcellulose, wherein the oral grain preparation is suitable for oral administration, and wherein the resulting outer layer does not contain a water-soluble cellulose polymer.

8. The oral grain preparation according to claim 7, wherein the anion exchange resin is 2-methylimidazole-epichlorohydrin copolymer.

9. The oral grain preparation according to claim 7, which is obtained by coating the plain grain with the solution of the water-soluble cellulose polymer at an amount of 3.5 to 8% by weight and then coating the plain grain with the aqueous dispersion consisting essentially of ethylcellulose at an amount of 0.5 to 4% by weight, wherein the total coating amount is 5.5 to 8.5% by weight based on the weight of the plain grain.

10. The oral grain preparation according to claim 7, which is obtained by coating the plain grain with the solution of the water-soluble cellulose polymer at an amount of 4 to 6% by weight and then coating the plain grain with the aqueous dispersion consisting essentially of ethylcellulose at an amount of 1 to 2% by weight, wherein the total coating amount is 6 to 8% by weight based on the weight of the plain grain.

11. The oral grain preparation according to claim 7, wherein the water-soluble cellulose polymer is hydroxypropylmethylcellulose, hydroxypropylcellulose, or methylcellulose.

12. The oral grain preparation according to claim 7, wherein the aqueous dispersion consisting essentially of the ethylcellulose is a latex aqueous coating agent containing ethylcellulose as a base material.

* * * * *